(12) United States Patent
Thorne, Jr. et al.

(10) Patent No.: US 8,449,521 B2
(45) Date of Patent: May 28, 2013

(54) METHODS FOR MAKING AND USING A VIAL SHIELDING CONVENIENCE KIT

(75) Inventors: Gale H. Thorne, Jr., Bountiful, UT (US); Gale H. Thorne, Bountiful, UT (US); Kendall P. Thorne, Layton, UT (US)

(73) Assignee: IntraVena, LLC, Bountiful, UT (US)

( * ) Notice: Subject to any disclaimer, the term of this patent is extended or adjusted under 35 U.S.C. 154(b) by 322 days.

(21) Appl. No.: 12/925,122

(22) Filed: Oct. 14, 2010

(65) Prior Publication Data

US 2011/0034899 A1 Feb. 10, 2011

Related U.S. Application Data

(63) Continuation-in-part of application No. 12/460,470, filed on Jul. 20, 2009, which is a continuation-in-part of application No. 12/319,326, filed on Jan. 6, 2009, now abandoned, which is a continuation-in-part of application No. 12/313,013, filed on Nov. 14, 2008, now abandoned, which is a continuation-in-part of application No. 12/080,185, filed on Apr. 1, 2008, now abandoned, which is a continuation-in-part of application No. 12/012,837, filed on Feb. 6, 2008, now Pat. No. 7,785,312.

(51) Int. Cl.
*A61M 5/32* (2006.01)

(52) U.S. Cl.
USPC ........... 604/411; 604/407; 604/408; 604/415; 206/570; 53/476

(58) Field of Classification Search
USPC .. 604/403, 407, 408, 411, 415, 416; 206/570, 206/571; 53/410, 476; 141/1
See application file for complete search history.

(56) References Cited

U.S. PATENT DOCUMENTS

| | | |
|---|---|---|
| 5,289,858 A | 3/1994 | Gravenkort |
| 7,758,560 B2 | 7/2010 | Connell et al. |
| 2009/0306621 A1* | 12/2009 | Thome et al. ................. 604/500 |

* cited by examiner

*Primary Examiner* — Emily Schmidt
(74) *Attorney, Agent, or Firm* — Gale H. Thorne

(57) ABSTRACT

Methods for making an using convenience kits for hazardous drug (liquid) transfer from vials to syringes and target IV connectors. The following methods for making and using are disclosed:
  (1) Using a conventional plastic bag as a vial and vial adapter enclosing shroud.
  (2) Using of a flange (i.e. latch arm) free vial adapter which may, therefore, be used for a large variety of vial sizes.
  (3) Providing a seal about an access hole through which a vial adapter dispensing portion provides a closed fluid dispensing pathway.
  (4) Using the shrouding bag and an associated elastic band to provide desired stability of a spiked vial.
  (5) Accessing, measuring and transferring vial contents directly from a vial to a target IV container.

15 Claims, 12 Drawing Sheets

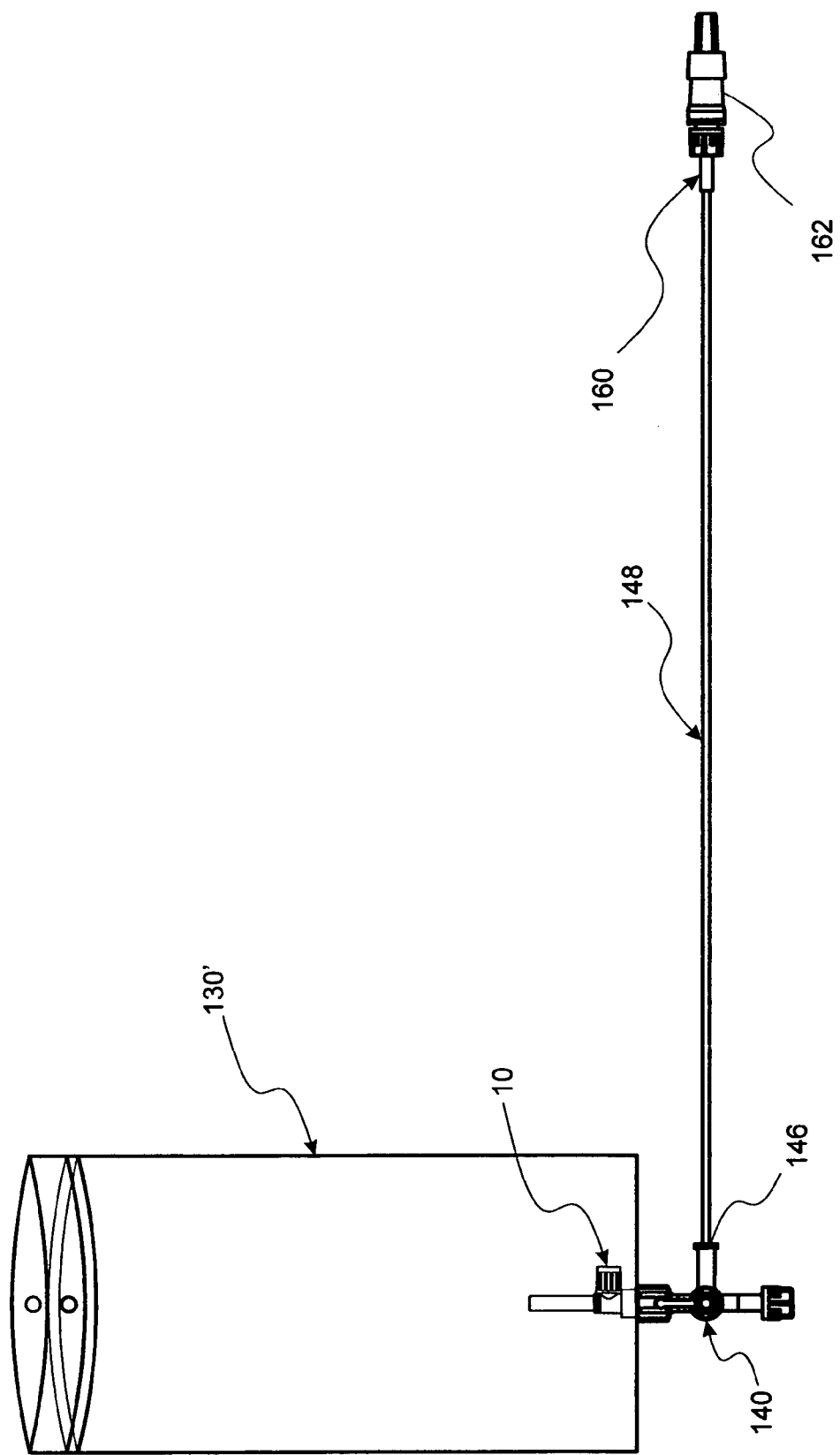

METHODS FOR MAKING AND USING A VIAL SHIELDING CONVENIENCE KIT

CONTINUATION-IN-PART

This Application for Patent is a Continuation-in-Part of U.S. patent application Ser. No. 12/460,470, filed Jul. 20, 2009, which is a Continuation-in-Part of U.S. patent application Ser. No. 12/319,326 filed Jan. 6, 2009, which is a Continuation-in-Part of U.S. patent application Ser. No. 12/313,013, filed Nov. 14, 2008, now abandoned, which is a Continuation-in-Part of U.S. Ser. No. 12/080,185, filed, Apr. 1, 2008, which is a Continuation-in-Part of U.S. patent application Ser. No. 12/012,837 filed Feb. 6, 2008, now allowed, the contents of which are made part of this Application by reference.

FIELD OF INVENTION

This invention generally relates to methods for making and using medical convenience kits and, more specifically, for making convenience kits which have a specific purpose of enclosing a vial to provide a closed system for transferring solutions from vials to IV dispensing systems used in patient drug delivery and especially for drug delivery using medicines which present a hazard if exposed to an open environment.

BACKGROUND AND DESCRIPTION OF RELATED ART

Philosophically and practically, a medical device, such as that embodying Applicant's invention, to be truly useful in modern contemporary practice must not only be considered safe and efficient, but must also be cost effective. There are many facets of related devices which affect cost effectivity. Such facets include product costs relative to value of treatment made possible by the device, cost of inventorying (e.g. how many parts or stock keeping units (SKU's) are necessary to keep in stock to cover possible uses of the device), risks associated with device use and ability of device makers to meet manufacturing standards established for the safety of a receiving patient. It is for this reason that Applicant's have elected to concentrate upon convenience kits assembled from products currently proved and certified as being safe and effective for medical use by manufacturers whose controls and procedures are also certified.

As an example, vial adapters are well known and widely available in contemporary medical commerce. Such vial adapters are available as vented and unvented models. Further, as vial adapters generally are not only used to provide access to vial contents by spiking a vial septum, but also to provide stabilizing flanges or latch arms which latch about cap and neck of a vial to securely affix the vial to the adapter. While such latch arms or stabilizing flanges have proved effective, vial adapters with such appendages must often be customized to meet different vial size requirements. This results in increases in numbers of SKU's required to meet needs of a variety of vial sizes used, increasing cost of handling and inventory. Such problems can be eliminated by finding a way to secure a vial to a vial adapter spike without requiring stabilizing flanges (or latch arms) thereby providing an opportunity to use a vial adapter that has universal application to a large range of vial sizes.

Related Art

U.S. patent application Ser. No. 12/460,470, from which the U.S. Patent Application continues-in-part, discloses problems associated with Hazardous Drug Handling and provides inventive solutions for those problems. This Patent Application incorporates by reference such disclosure and other information relative to specifying configurations for shrouding vials preparatory to drug transfer.

U.S. Pat. No. 7,758,560 B2 issued Jul. 20, 2010 to Edward G. Connell, et al. ("Connell") and titled HAZARDOUS MATERIAL HANDLING SYSTEM AND METHOD discloses a method and system for handling hazardous materials contained in a vial. The system includes an isolation enclosure having an opening for selectively sealing about a vial; the enclosure being made up of a cap portion and a bag body portion. Inside the enclosure is an extraction member (vial adapter) having a preceding engaging member and a primary engaging member which include a plurality of latch arms for securing the vial to the extraction member in two separate steps taken before and after spiking the vial, respectively.

As seen in FIGS. 2 and 3 of Connell, enclosure 14 comprises a body portion 16 and a cap portion 17. Body portion 16 is taught to be a flexible bag which is affixed to cap portion 17 to form impermeable enclosure 14. Cap portion 17 is taught to be constructed of rigid material having an inlet port 18 and an outlet port 19. Inlet port 18 comprises a male connector for connecting to a connecting member 52 on the distal end of body portion 40 (a dispensing portion of a vial adapter). Outlet port 19 comprises a female connector for connecting to a valve component (e.g. needleless connector) 54. Ports 18 and 19 provide an exit pathway from enclosure 14. Clearly, ports 18 and 19, while providing an exit pathway, also add what is generally known as "dead space" by requiring an additional volume of liquid to be delivered from a vial to the valve component when compared to a simpler direct attachment between a vial adapter and an exit valve (needleless connector) which is commonly found in vial adapters securely affixed to needleless connectors in parts contemporarily commercially available.

The vial adapter of Connell, referenced as engaging member 34 is taught and claimed to have a plurality of latch arms for engaging a vial when first inserted into enclosure 14 at a first site which is distant from a vial spike such that closure of body portion 16; then, after bag closure, for engaging the vial at a second site whereat the vial is spiked. In this way, the following two things are apparently accomplished: (1) no emissions from spiking are possible until the bag is closed and (2) the vial spike is not inadvertently contaminated by contact with an unsterile vial exterior during vial insertion, a problem which must be solved by any closed vial adapter spiking process. The latching arms, themselves, apparently provide for stabilizing the vial inside an enclosure having a base made of a hard plastic shell.

Connell teaches both an unvented vial adapter and a vented vial adapter. The valve affixed to outlet port 19 is commonly known as a CLAVE® needleless connector. Connell further teaches a needleless connector adapter 62 which may be used with a syringe and to the CLAVE® valve to permit flow between the syringe and vial adapter, when attached, and restrict flow from each separated part when adapter 62 is separated from the CLAVE® valve.

U.S. Pat. No. 5,289,858 issued Mar. 1, 1994 to Rich W. Grabenkort (Grabenkort) and titled SYSTEM FOR ACCOMMODATING WITHDRAWAL OF LIQUID FROM A BULK SUPPLY discloses providing a safety enclosure for measuring and transferring liquid from a bulk container to a desired site of use or conveyance. The system is taught to be used with a highly commercially successful Add-Vantage® brand bulk drug reconstitution system sold in the United States. Mixing drug and diluent is taught to be accomplished within the bulk container, which provides a reservoir for the mixture in a bag 20. System 10, the subject of the titled invention, is connected with bag 20 through a connecting means 50 to a conduit 56. Conduit 56 is interrupted by a one-way valve 102 which prevents backflow into bag 20. A syringe is taught to be engaged in communication with conduit 56 through a "Y" connector 108 and a second connecting means 116 which is a valve that is closed when the syringe is separated therefrom.

The "Y" site is further connected to a conduit 132 which is also interrupted by a one-way valve. Conduit 132 is also interrupted by a stopcock 180 which may be switched to direct flow to a waste chamber 140 or to a drug receiving site. It is important to note that stopcock 180 is specifically provided for selection of a conduit to either direct flow from a syringe to a waste container or to the drug receiving site. It is also important to note that, due to the disposition of the one way valves, the syringe may be used as a pump to successively deliver liquid from bag 20 to a delivery site without rotating a pathway selecting member of stopcock 180. Stopcock 180 provides no valvular control of fluid flow between the source reservoir and the syringe during the pumping process.

Prevention of backflow by valve 102 provides the necessity for waste chamber 140, as excess liquid or air drawn into the syringe cannot be returned to bag 20. To provide for opportunity to deliver only a desired dose of liquid from the syringe, any excess fluid drawn into the syringe must be wasted. This is the reason for application of stopcock 180, to provide a selectable pathway to a waste chamber 140 because there is no return pathway to bag 20.

To provide access to bag 20 and other associated parts prior to drug transfer and to provide a flexible safety barrier an invertable bag 80 (i.e. one which may be in a given orientation to provide access to bag 20 and associated parts in one retracted state and extended (turned inside out) to envelop bag 20 and associated parts in another state) is taught and claimed. In this case, a vial 12 is connected to a bag 20 and no fluid is exchanged before bag 20 is inverted. Bag 20 is shown to be sealed about conduits 56 and 132 to provide a closed environment for bag 20 and associated parts once bag 80 is inverted and sealed superiorly. When inverted, the bag 80 is also taught to enclose waste receptacle 140. In FIGS. 6 and 7 of Grabenkort, it is shown that slider clamps may be used in place of the stopcock.

While Connell and Grabenkort both disclose systems and methods for enclosing a source of medication prior to access and delivery of such, problems of numbers of SKU's, fluid (i.e. drug) handling efficiency and development of specialized parts should be considered relative to novelty of Applicant's invention.

Terms and Definitions

In the following table 1 is a list of terms and associated definitions provided to improve clarity and understanding of precepts of the instant invention:

convenience kit, n, a medical device kit as defined by the United States FDA.
effluent, n: something that is emitted (flows out), particularly, from a vial.
fluid, n: a gas or liquid.
flush syringe, n: a syringe, pre-filled with a predetermined volume of flush solution.
HD, n: hazardous drug.
IV set, n: intravenous drug delivery tubing specifically dedicated for use with an associated IV catheter and IV container.
N container, n: a container, made of glass or plastic in the form of a bottle or N bag used to hold and deliver N fluids containing medications for delivery through an N.
kit, n: a group of parts, provided within a single package for a designated medical use luer fitting, n: a medical connector which is in common use in medical practice.
luer locking connector, n: a connector associated with a luer fitting having a locking mechanism whereby a male and female connector are securely, but generally releasibly affixed one to the other.
needleless connector, n: a fitting which permits needle free fluid access to an IV set or through a vial adapter and which has interface geometry similar to a conventional syringe
port, n: a site for a medical connector, where through fluid is communicated.
shroud, n: a vial and vial adapter containing cover which provides a barrier against fluids emitted from a vial septum during fluid acquisition from the vial.
SKU, n: stock keeping unit, an inventory term related to shelf quantities of a required product.
subassembly, n: a part of an assembly.
subsystem, n: a part of a system.
unitized, adj: a plurality of separate parts permanently joined to be used as a single unit.
vial, n: a medication container in which medication is delivered from a manufacturer to a medical facility, fluid in the vial is usually accessed via a spike of a vial adapter which pierces a septum of an exposed diaphragm of the vial.

Table 1

BRIEF SUMMARY AND OBJECTS OF THE INVENTION

In brief summary, this novel invention provides a basis for making and using vial adapter shrouding subsystems which may be sealed once a vial is disposed within an integrally associated shroud to provide a closed transfer system. Generally, the instant invention as disclosed herein, is a method or process for making and using a device embodied in convenience kit products. Such products are generally combinations of conventional, selected components which have been proved and certified for medical use.

The method for making and using a sealable vial adapter enclosing safety shield subassembly according to the instant invention generally involves the following:
Selecting and Making use of the Following Commercially Available Medically Certified Products (a) preferably, a vented vial adapter having a vial spike for piercing a vial septum on a proximal end and a fluid dispensing portion on the opposite or distal end and also preferably with a vented vial adapter having an installed removable cover for the vial spike. The vial adapter preferably is without vial securing latch arms or vial attachment flanges, although adapters having such attachment arms may be used within the scope of the invention. As is true of substantially all vial adapters, the fluid dispensing portion is a hollow tube having internal geometry consistent with a female luer fitting and an exterior cylindrical surface distally ending at outwardly protruding flanges structured for mating with a male luer locking connector;

(b) a fluid valving device (such as a needleless connector or a stopcock) which has a male luer fitting and a luer locking connector which provides a luer locking interface for flanges and geometry of the female luer fitting of the associated vial adapter;

(c) a hollow cylindrical elastic gasket or collar having an internal diameter which is sized to fit tightly about the outer surface of the vial adapter fluid dispensing portion when relaxed but having sufficient elasticity to be stretched without permanent deformation to be displaced over the flanges at the end of the dispensing portion, The gasket has proximal and distal edges defining a length which is less than the length of the cylindrical outer surface of the dispensing portion and a wall thickness which is sized to interact circumferentially with the male luer locking connector of the fluid valving device; and (d) a conventional plastic bag which is sealable (e.g. by a zipper seal) for complete bag closure at an otherwise open end of the bag is preferably employed for the shroud. For convenience of use, after assembly and insertion of a vial into the bag, a hang hole may be provided proximal to the sealable portion (i.e. between the sealable portion and the top) of the bag for hands free operation.

Providing the Following Assembly Tools:

(e) gasket or collar expanding and bag puncture tooling by which the gasket is elastically expanded to be displaced over the dispensing portion flanges (This tooling may comprise a tool having a cone shaped proximal end, a base of the cone being approximately the same diameter as the outward extension of the dispensing portion flanges with the associated point of the cone being blunted for assembler safety, yet sharp enough to pierce a hole in the plastic bag which is displaced over the flanges and about the dispensing portion. On the distal end, this tool preferably has a cylindrical rod portion which is sized and shaped to fit into the female luer orifice of the vial adapter.); and (f) an assembly fixture upon which the vial adapter may be disposed during assembly, the fixture preferably having complementary slots and holes for stabilizing and releasibly mounting the vial adapter and a breadth and width sized to allow facile displacement of the bag there over.

Then, Assembling the Subassembly as Follows:

(g) disposing the vented vial adapter onto the assembly fixture oriented to provide access to the dispensing portion;

(h) inserting a portion of the gasket expanding tool into the female luer fitting of the dispensing portion of the vial adapter for use thereof;

(i) using the gasket expanding tool, elastically expand and displace the gasket over the flanges and to thereby be disposed in a relaxed state in tight communication with the outer surface of the dispensing portion of the vial adapter at a site where the edge of the gasket closest to the flanges is sufficiently close to the flanges to communicate with a male luer connector later affixed to the flanges (It is preferred to apply adhesive to gasket and dispensing portion to securely affix the gasket to the dispensing portion; however; it is also preferred to use an adhesive which takes sufficient time to cure to permit connecting of an associated male luer connector before the adhesive sets.);

(j) displacing the open end of the bag over the fixture such that the end of the bag opposite the open end communicates with the exposed point of the collar expanding tool;

(k) drawing the bag over the point to create a hole in the bag which is sufficiently large to permit the bag to be displaced over the flanges yet which is smaller than the diameter of the cylindrical outer surface of the gasket (It is important to note that when gasket and hole are disposed together, thickness of the gasket at the communicating edge of the gasket should entirely be in communication with the circumferential edge of the hole);

(l) displacing the collar expanding part from the dispensing portion;

(m) disposing the male luer fitting into the female luer fitting to make a secure fluid connection; and (n) securely affixing the luer locking connector in tight communication with the flanges on the dispensing portion, thereby forcing the gasket proximally against frictional forces to assure a sealing interface between luer locking connector, bag and gasket to ensure, after closing the zipper seal of the bag and then spiking a vial with the vial spike, vial originated effluents, other than fluid delivered through the fluid dispensing portion, are fully contained within the bag (It is preferable to apply adhesive between the male luer locking connector and flanges to assure a secure connection. Note, there are two seals made by this connection. First, a fluid tight seal is provided for fluid flow from vial through luer fittings and, second, a seal is made about the hole in the bag to contain, within the bag, all material which does not flow through the luer fittings, but which is otherwise emitted from the vial.

To complete this assembly process, an appropriate fluid valving device, having the male luer locking connector cited supra, should be selected and made part of the subassembly. Though other fluid valving devices may be used within the scope of the invention, a selected device may be a needleless connector or a stopcock. If a needleless connector is used, medical or pharmaceutical use of the device is substantially the same as that of a conventional vial adapter/needleless connector currently commercially available.

If a flow-path selecting valve (such as a stopcock) is used, a measurement syringe may be used to communicate with one port of the valve. To another port of the valve, an extension set may be affixed to communicate therefrom to a deliverable IV container. A third port should have the male luer locking connector and be securely affixed to be unitized with the dispensing portion of the vial adapter. So connected, it is important that the syringe communicates with the dispensing portion of vial adapter in one valve state for drawing and measuring a dose from the vial. For conventional dose measurement, flow through the pathway of the dispensing portion should be bidirectional to permit gas and excess liquid to be returned to the vial, leaving the desired dose in the syringe for delivery to the target IV container. Note, when a flow-path selecting valve is used, the syringe need not be removed from being affixed to the associated valve port and each dose from a vial is displaced through a closed system to the target IV container.

Packaging and Sterilizing

Once so assembled the unit is packaged and sterilized for ultimate transport and use. It is preferable to complete the packaged assembly by including an elastic band (preferably non-latex) within the package to be used as disclosed in detail hereafter.

Modes of Using the Invention

It is important to note that the shroud provides protection from hazardous material which may be on the outside of the vial, for gas or aerosols emitted upon vial spiking or for leakage and spills due to vial septum or other container failure. To guard against contact with matter on the exterior of vial, it is recommended that all actions relative to accessing and drawing fluids from a vial be performed within the safety of the sealed enclosure provided by the shroud.

For a latch arm free vial adapter, vial handling and accessing are quite independent of vial size and form of the valve affixed to the dispensing portion of the vial adapter. Each vial is generally prepared for fluid transfer using the following steps:

(a) Removing the subassembly from the package.

(b) If the septum of a selected vial is to be cleaned after the vial is introduced into the shroud (preferred), displacing a wipe, such as an alcohol wipe into the shroud.

(c) Preferably holding the wipe from falling from the shroud, displacing a selected vial (handled with care according to institutional protocol) into the shroud.

(d) Closing and sealing the shroud. (At this time, before the vial septum is spiked, it is considered good practice to test the seal of the shroud by gently squeezing the shroud and being sensitive to a reduction in pressure within the shroud).

(e) If a cap on the vial has not been removed, removing the associated cap from the vial digitally through the bag.

(f) Also, if septum cleaning needs yet to be done, accessing the wipe through the bag and cleanse the septum (e.g. by wiping).

(g) Removing the cover from the vial spike. (This act is easily performed by telescoping the shroud (e.g. plastic bag), grasping the cover and displacing the shroud in a direction which removes the cover from the spike).

(h) If the subassembly is to be used in a handheld mode, securing the spike in the vial by folding the shroud tightly about the vial and binding the enclosed elastic band about shroud and vial to thereby secure the vial adapter to the vial.

(i) If the shroud is provided with a hang hole and it is desired to use the subassembly in a hands free mode, without folding the shroud, wind the elastic about vial and shroud to provide vial support.

Thus, depending upon the valve selected and affixed to the dispensing portion of the vial adapter, use of the completed assembly varies.

If a Needleless Connector is Affixed to the Vial Adapter, Steps for Using the Subassembly Comprise:

(1) Attaching a measurement syringe (and, as desired, a needleless [and preferably dripless] connector adapter) to the needleless connector;

(2) Drawing and measuring a desired dose sample into the syringe;

(3) Disconnecting the measurement syringe (and needleless connector adapter) from the needleless connector; and (4) Transporting the dose filled syringe to a site of use. (Note that the above four steps are commonly used in contemporary medical-vial-acquisition devices.)

If a Flow-Path Selecting Valve (e.g. a Stopcock) and Associated Extension Set are Affixed to the Dispensing Portion of the Vial Adapter, Steps for Using the Assembly Comprise:

(1) Attaching a measurement syringe to a predetermined port of the flow-path selecting valve;

(2) Attaching an output connector of the associated extension set, affixed to an output port of the flow-path selecting valve, to a target IV container;

(3) Selecting a flow path of the path selecting valve to provide a communicating pathway between the vial and measurement syringe;

(4) Drawing and measuring (returning undesirable quantities of fluid through the dispensing portion of the vial adapter) a desired dose of medicine from a vial affixed to the vial adapter shielded by the shroud;

(5) Selecting another flow path of the path selecting valve to provide a communicating pathway between the syringe and target IV container; and (6) Dispensing the desired dose into the IV container.

It is important to note that a disconnection of the assembly from the IV container must be made for delivery of the target IV container to a site of use. For this reason, a connecting device, such as a needleless connector adapter (e.g. a Texium® or Spiros®) or a flush syringe attachment may be provided at the end of the extension set where connection is made with the target IV container to provide safety when disconnecting thereat.

Accordingly, it is a primary object to provide methods for making and using vial adapter enclosing safety shield convenience kits.

It is an important object to utilize a conventional, commercially available vial adapter and other commercially available proved and medically certified components.

It is a critical object to provide a sealable enclosure for the vial adapter such that the vial adapter may be a vented vial adapter.

It is also an important object to provide methods for making and using vial adapter enclosing safety shield convenience kits which do not require vial attachment flanges or latch arms to thereby reduce SKU and kit cost and broaden opportunity for use of conventional vial adapters.

It is a principle object to provide a vial adapter enclosing safety shield convenience kit in which dispensing portions of the vial adapter are directly connected to a fluid communicating device, as is commonly the case for conventional vial adapter/needleless connector interfaces.

It is an object to provide a vial adapter enclosing safety shield convenience kit which utilizes a needleless connector as the fluid communicating device.

It is another object to provide a vial adapter enclosing safety shield convenience kit which utilizes a stopcock as the fluid communicating device.

It is another principle object to provide a method for sealing a hole in a plastic bag disposed about a fluid dispensing portion of a vial adapter such that the bag, once closed at an entry portal for displacing a vial into the bag, provides a sealed, closed enclosure for safety in vial content access.

It is another important object to provide a method for using a conventional plastic bag as the shield in a vial adapter enclosing safety convenience kit.

It is yet another object to provide a vial adapter enclosing safety shield convenience kit which may be used to access fluid from a vial via a measurement syringe and deliver such fluid to an IV container without disconnecting the syringe from a communicating connection with the vial adapter enclosing safety shield.

It is another object to provide a bag with a hang hole such that the vial adapter enclosing safety shield convenience kit may used in a hands free mode.

It is a consequential object to unitize parts within the vial adapter enclosing safety convenience kit to improve safety during use.

These and other objects and features of the present invention will be apparent from the detailed description taken with reference to accompanying drawings.

BRIEF DESCRIPTION OF THE DRAWINGS

FIG. 14 is a front elevation of the subassembly seen in FIG. 12 with an extension set affixed to the stopcock.

DETAILED DESCRIPTION OF THE ILLUSTRATED EMBODIMENTS

In this description, the term "proximal" indicates the segment of the device normally closest to the object of the sentence describing its position. The term distal refers to a segment oppositely disposed. Reference is now made to the embodiments illustrated in FIGS. 1-19 wherein like numerals are used to designate like parts throughout. For parts which are similar but not the same as parts originally specified with a given number, a prime of the original numbers is used. It is important that all parts selected for use in convenience kits associated with the instant invention, be able to be sterilized, for example, by such methods as gamma radiation.

Methods of Assembly

Figure 1:
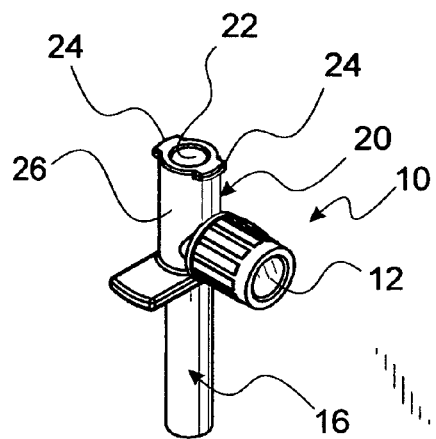
FIG. 1 is a perspective of a vented vial adapter which may be used as part of a convenience kit, an associated spike of the vial adapter being hidden by a cover.

Reference is now made to FIG. 1 wherein an exemplary vial adapter 10 is seen. Vial adapter 10 is representative of many commercial vial adapters which may be used within the scope of the invention. Exemplary vial adapter 10 has a filtered vent 12 through which air is drawn (or emitted) to permit a gas exchange for fluids exchanged with an associated vial. (Other non-vented vial adapters may be used within the scope of this invention.) Also vial adapter 10 has a spike 14 (not seen in FIG. 1, but seen in FIG. 13). In FIG. 1, spike 14 is covered and protected by a removable cover 16 to protect sterility of spike 14 until time spike 14 is bared for the purpose of spiking a vial septum. It is critical that spike 14 be so covered initially, not only to protect sterility of spike 14, but also to obviate inadvertent spiking of sides of a shroud (e.g. a bag) in which vial adapter 10 is enclosed.

Vial adapter 10 also comprises a fluid dispensing portion 20 where through fluids are generally dispensed from a spiked vial. Portion 20 comprises a hollow tubular shape which extends distally to a female luer fitting 22 and associated connecting luer lock flanges 24. Proximal to flanges 24, portion 20 comprises a rounded surface 26 which is generally cylindrical in shape and of predetermined diameter. Exemplary vial adapter 10 may be a B/Braun mini-spike vial adapter product number S4003231 (or S4003400 if purchased before sterilization). It should be noted that most vial adapters have similarly configured dispensing portions.

Figure 2:
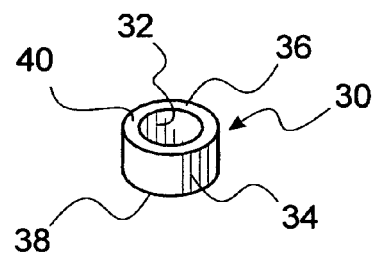
FIG. 2 is a perspective of a gasket or collar used in conjunction with a vial adapter, such as the vial adapter seen in FIG. 1, to provide closure and a seal about a hole in a bag.

Reference is now made to FIG. 2 in which a gasket or collar part 30 is seen. Gasket part 30 is a hollow cylindrical part which is defined by an internal surface 32 and an exterior surface 34. Length of part 30 is limited by a top edge 36 (as seen in FIG. 2) and a bottom edge 38. Both of such edges should be made smooth and even. A wall 40 having a thickness which is defined by the difference in diameter of surface 32 and surface 34. Gasket part 30 may be made by slicing a predetermined length of medical grade elastic tubing having an internal diameter which fits snugly about rounded surface 26 and a wall thickness which is greater than outwardly protruding length of flanges 24. Note that gasket part 30 must be sufficiently elastic to be stretched to be displaced over flanges 24 and sufficiently elastic to become snugly disposed about rounded surface 26 once disposed thereon. Material from which gasket part 30 may be made is medical grade extruded PVC (poly vinyl chloride) tubing.

Figure 6:
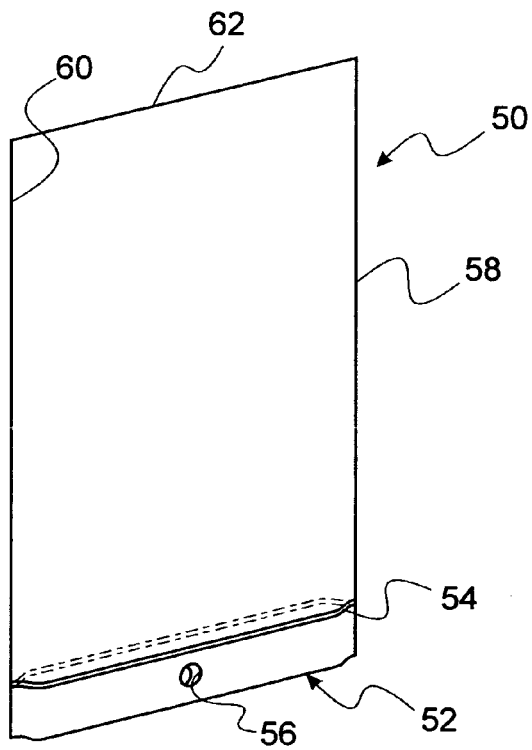
FIG. 6 is a perspective of a conventional plastic bag with a zipper closure and a hang hole.

A conventional zippered plastic bag 50 is seen in FIG. 6. While it is preferred to use a zippered bag, any bag which is open only at one end and which is close able to isolate bag contents from the surrounding environment may be used within the scope of the instant invention. However, it is of fundamental importance to note that a selected bag should not only be made of medically approved material, but also should be commercially available in sufficiently large commercial volume to assure a low manufacturing cost. Such a bag may be a 4×8 inch, 2 mil bag, such as product number F20408H, 2 mil bag with hang hole from Discount Plastic Bags. A similar bag, but being made from 4 mil material may be acquired from GT Bag Company via part number G4ph4x8. Both Discount Plastic Bags and GT Bag Company may be contacted via the internet. Bag size may also be varied (e.g. a 5×8 4 mil hang hole zipper bag).

Referring again to FIG. 6, bag 50 has an open end 52 whereat a zipper seal 54 is disposed to provide closure for bag 50. Preferably, a hole 56 is disposed between end 52 and seal 54. Otherwise, bag 50 is closed along sides 58 and 60 and bottom 62.

Figure 4:
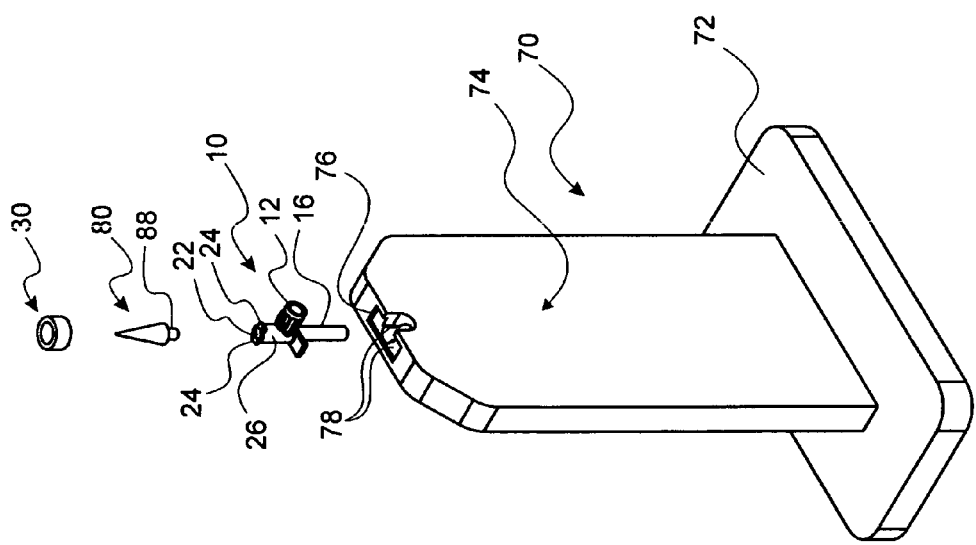
FIG. 4 is an exploded perspective of an assembly fixture, a vial adapter (seen in FIG. 1), a bag puncture and expander tool and a gasket (seen in FIG. 2).

To provide stability for assembling a convenience kit as an inventive product of the instant invention, a stand 70, seen in FIG. 4, may be provided. Stand 70 has a stabilizing base 72 from which an upright assembly support 74 extends to a topmost section 76. Within section 76 a set of holes and groves 78 are provided which are complimentary to cover 16 and filtered vent 12 of vial adapter 10. Stand 70 may be made from any material which is sufficiently rigid to withstand assembly and which can be sterilized and used in a medical assembly environment.

Figure 3:
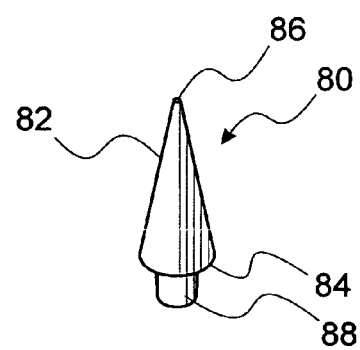
FIG. 3 is an expander tool providing tooling for use in displacing the gasket about a dispensing portion of the vial adapter and for making a hole in the bag.
Figure 5:
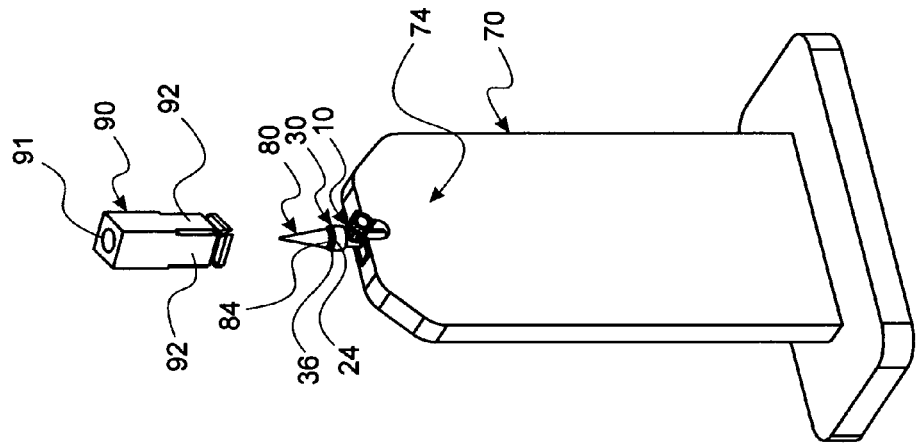
FIG. 5 is a perspective of the assembly fixture with the vial adapter (see FIG. 1) disposed therein, and with the gasket (see FIG. 2) displaced over the puncture and expander tool (see FIG. 3) to be disposed about a dispensing portion of the vial adapter. Also a tool for forcing the gasket over the puncture and expander tool is seen to be superiorly disposed above the assembly fixture and associated parts.

One other part which is important in initial steps of an assembly of a convenience kit of the instant invention disclosed herein is a puncture and expander tool 80 seen in FIG. 3. As seen FIG. 3, the upper portion 82 of tool 80 is cone shaped, extending upward from a base segment 84 to a point 86. In manufacture, point 86 should be blunted to obviate inadvertent injury to skin of a user. Extending downward from base segment 84 is a cylindrical rod 88 which has a diameter consistent with facile insertion into female luer fitting 22 of vial adapter 10. When disposed, as seen in FIG. 5, base segment 84 is broad enough in girth to expand a part, such as gaslet 30 to be displaced over flanges 24 of vial adapter 10.

Referring once more to FIG. 4, assembly begins by inserting vial adapter 10 (i.e. cover 16) into complimentary holes and grooves 78 in stand 70. Rod 88 of puncture and expander tool 80 is next inserted into female luer fitting 22 of adapter 10. Gasket 30 is next disposed upon puncture and expander tool 80 and displaced over flanges 24 of adapter 10. A forcing tool 90, having a centrally disposed through hole 91 and displaceable legs 92 is seen in FIG. 5. Such a tool may be used to forcibly displace gasket 30 over flanges 24. Gasket 30 is seen so disposed in FIG. 5. It should be noted that gasket 30 should be disposed past flanges 24 just far enough to permit a male luer locking connector to engage flanges 24.

Figure 7:
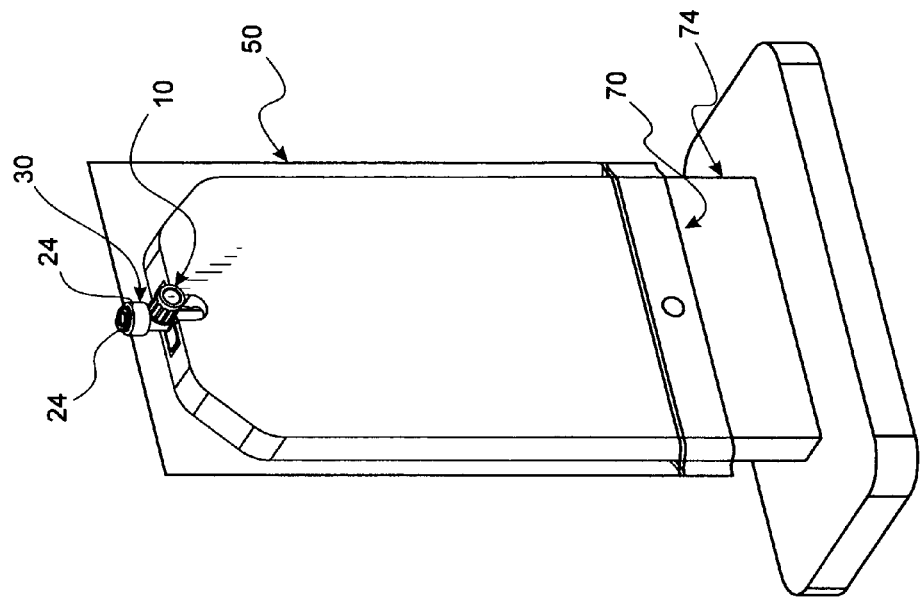
FIG. 7 is a perspective of the apparatus seen in FIG. 5 with the bag seen in FIG. 6 displaced over the assembly fixture to have a hole perforated therein by the puncture and expander tool.
Figure 8:
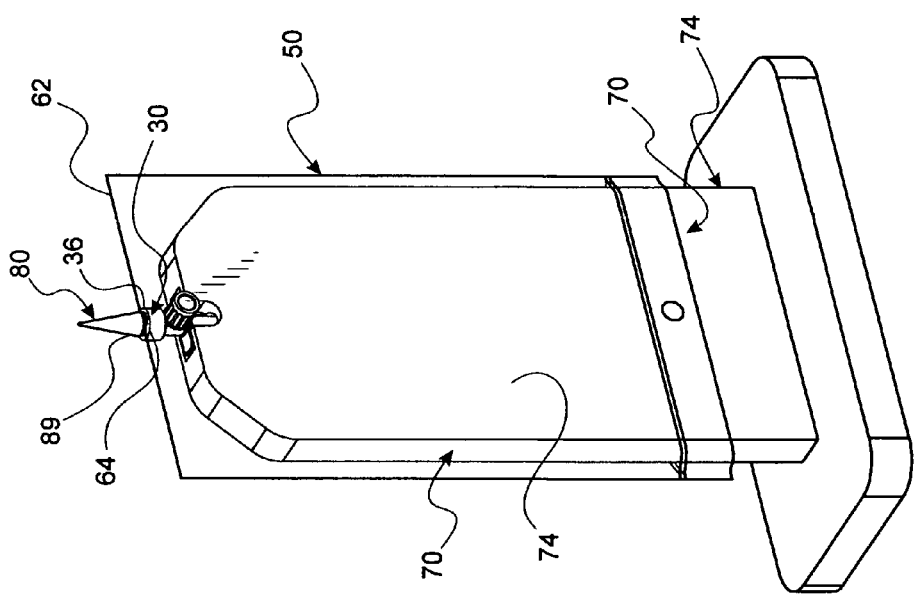
FIG. 8 is a perspective of the apparatus seen in FIG. 7 with the puncture and expander tool removed.

Next, a plastic bag (such as bag 50 seen in FIG. 6) is disposed about upright assembly support 74 of stand 70. Bag 50 is pulled downward until bottom 62 of bag 50 is punctured by puncture and expander tool 80 and until bottom 62 is in communication with gasket 30 creating a puncture hole 89, as seen in FIG. 7. Tool 80 is then removed, as seen in FIG. 8.

As seen in FIGS. 9-11 and 12, a fluid communicating device (such as needleless connector 100, seen in FIG. 9) having a luer locking connector 110 is then securely affixed to flanges 24. So connecting luer locking connector 110 to flanges 24 not only provides a selectively closed pathway for fluid dispensed from a vial, but also compressively communicates with bottom 62 of bag 50 and against gasket 30 such that a seal is made about hole 89 made in bag 50 by tool 80.

Figure 13:
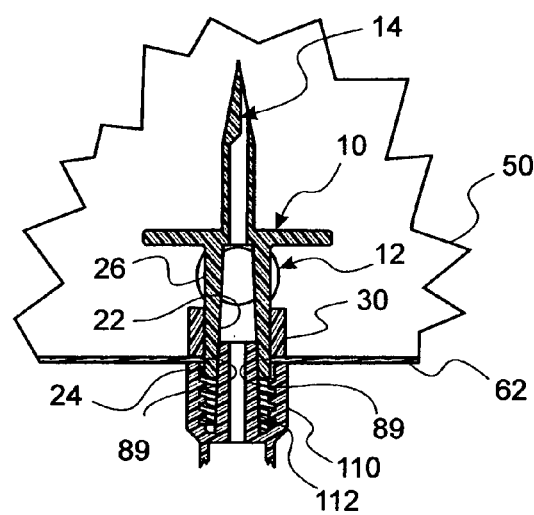
FIG. 13 is a segmented cross section of the vial adapter with spike cover removed, a portion of the bag, the gasket and a luer fitting associated with an attached valve device.

Formation of the seal about hole 89 in the bag is better seen in FIG. 13. Note gasket 30 is disposed about dispensing portion 26 of vial 10 such that when luer locking part 110 is tightly secured to flanges 24 (after a male luer fitting 112 is appropriately engaged in female luer fitting 22). This securing compressively secures bag bottom 62 about hole 89. It is preferred to addhesively secure both gasket 30 to dispensing portion 26 and luer locking connector 110 to flanges 24 to unitize parts of each associated convenience kit.

Figure 10:
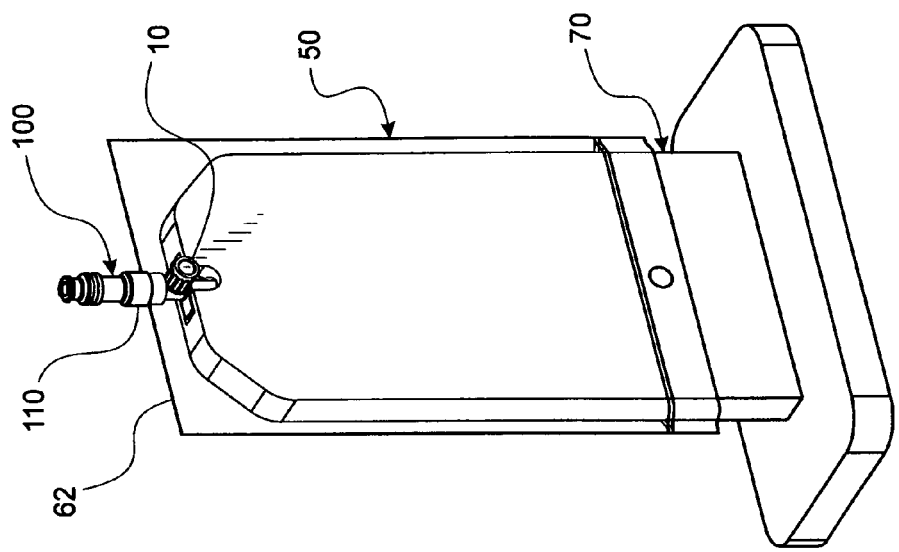
FIG. 10 is a perspective of a completed subassembly of the parts seen in FIG. 9.
Figure 9:
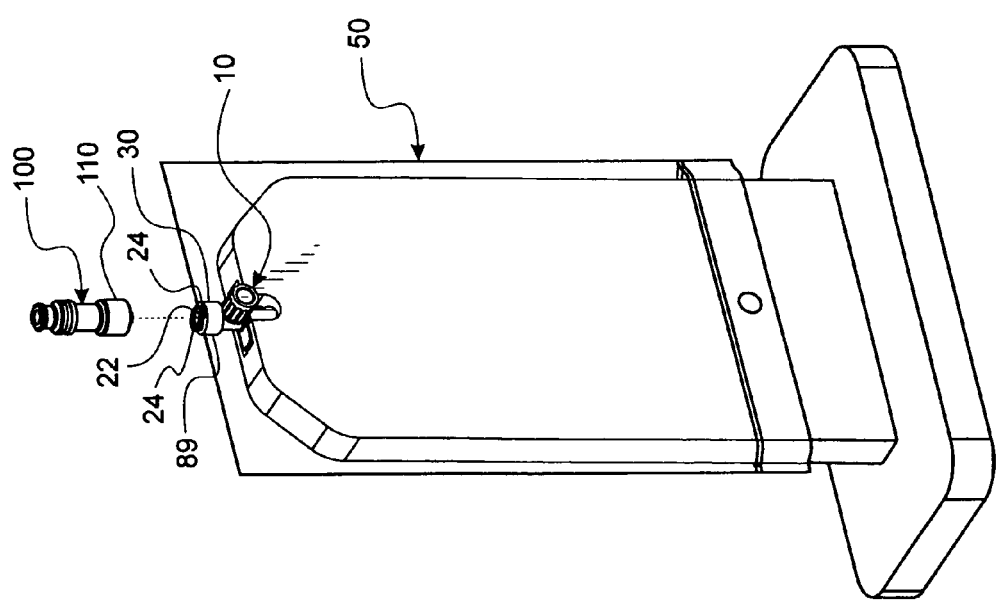
FIG. 9 is an exploded perspective of the apparatus seen in FIG. 8 and a needleless connector disposed for connection to the vial adapter.
Figure 11:
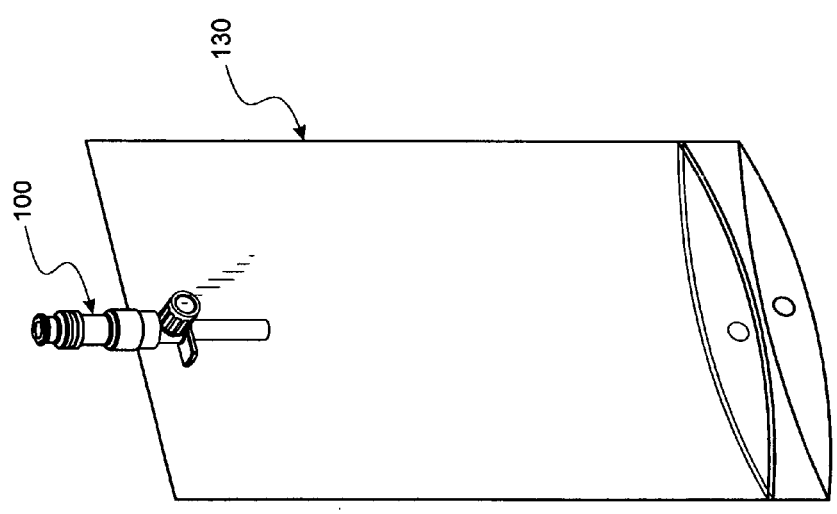
FIG. 11 is a perspective of the completed subassembly seen in FIG. 10 removed from the assembly fixture.

A completed subassembly 130 with a needleless connector affixed to vial adapter 10 is seen in FIG. 10. In FIG. 11, subassembly 130 is removed from stand 70 preparatory to packaging and final assembly of a convenience kit containing subassembly 130.

Figure 12:
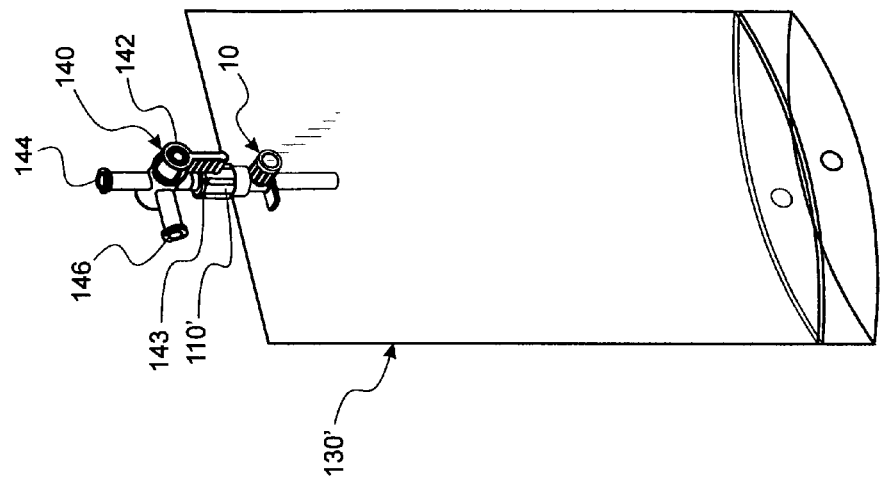
FIG. 12 is a perspective of an subassembly similar to the subassembly seen in FIG. 11, but with a stopcock affixed to the vial adapter rather than needleless connector.

Reference is now made to FIGS. 12 and 14 where assembly of a second subassembly 130' made in accordance with the instant invention is seen. Note, in FIG. 12, that a stopcock 140 having a male luer locking connector 110' is securely affixed to vial adapter 10 in the same manner, with the same mechanics, as luer locking connector 110 of needleless connector 100 is affixed. Pathway control by stopcock 140 is provided by a rotary, flow path "off" switch 142, as is the case for most medical stopcocks. Stopcock 140 is preferably a two position stopcock having one male luer locking connector 110' portal 143 and two luer locking female portals 144 and 146.

Further, to complete subassembly 130', an extension set 148 is affixed to stopcock portal 146, as seen in FIG. 14. Extension set 148 provides a pathway for fluids accessed from a vial with stopcock 140 in a first switched state and dispensed through the pathway with the stopcock in a second switched state.

In one preferred embodiment, as seen in FIG. 14, end 160 of extension set 148 may be fitted with a male needleless connector (preferably dripless) adapter 162. Male needleless connector adapter 162 may be a Texium, available from Carefusion, Inc. or a Spiros, available from ICU Medical.

Figure 19:
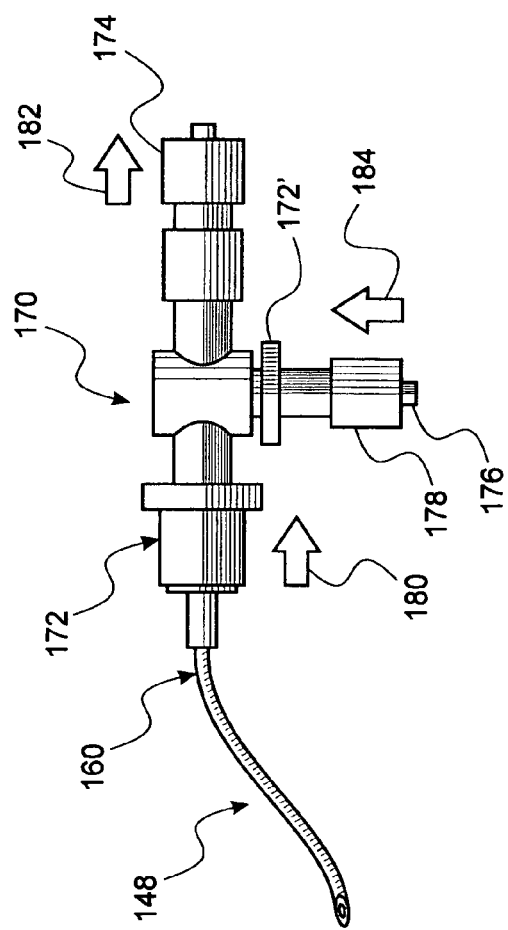
FIG. 19 is a frontal elevation of a section of an IV connector connecting end of an extension set affixed with appropriate connectors for attachment of a flush syringe.

It may be preferable for a using clinician to flush a connection to a target IV container before disconnecting rather than using a needleless connector adapter as seen in FIG. 14. For such a purpose, a dual one way valve 170, or equivalent valving, may be affixed to end 160 of extension set 148 as seen in FIG. 19. Dual one way valve 170 comprises a first one way valve 172 and a second one way valve 172'. As commercial dual one way valves generally have a female luer fitting as an output port, a male/male luer fitting 174 is affixed to the output port of valve 170 to provide a male luer interface connection for an attached IV container. A male luer fitting interface 176, preferably with luer locking connector 178, is provided for a flush syringe connection. So configured, valve 170 delivers the dose from an associated measurement syringe through one way valve 172 in direction of arrow 180 and to the attached IV container in direction of arrow 182. After delivery of the dose, a flush syringe affixed to fitting interface 176 is actuated to deliver flush in direction of arrow 184 and then to the associated IV container in direction of arrow 182 to cleanse the connection between male/male luer fitting 174 and the IV container. Such flushing is considered an effective method for clearing luer fittings of undesirable contamination.

Methods of Use

Figure 15B:
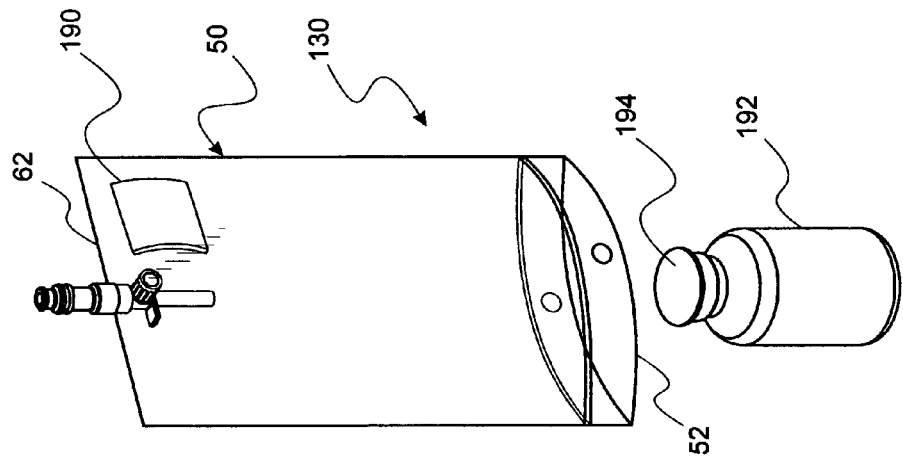
FIG. 15B is a perspective of the subassembly seen in FIG. 15 in more detail where in the bag is inverted, the swab is being maintained at the bottom (distal end of the bag) and the bag, being opened at the proximal is being displaced about a vial.
Figure 15A:
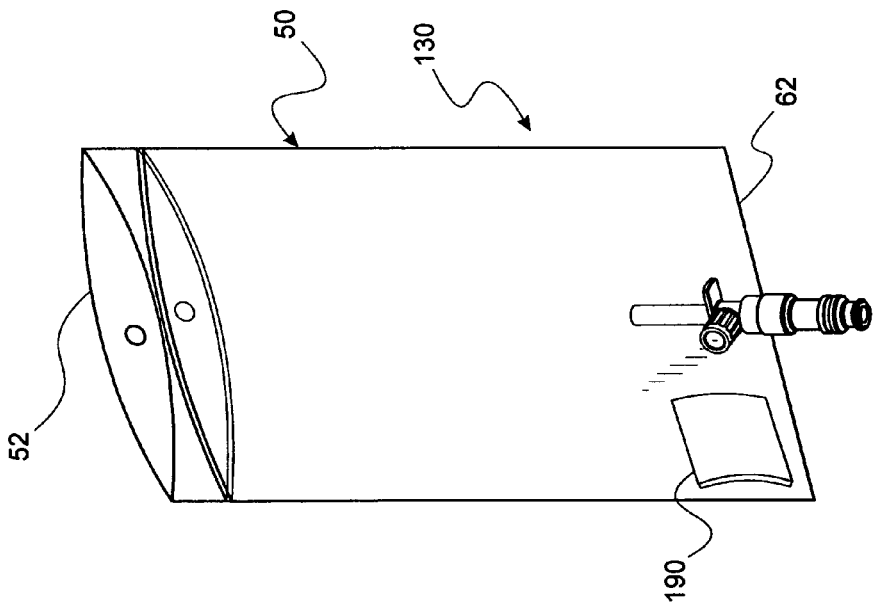
FIG. 15A is a perspective of a portion of the subassembly seen in FIG. 11 with the bag opened at a proximal end such that a disinfectant swab has been introduced therein.

Referring to FIGS. 15A-15G, an exemplary subassembly 130 is seen taken from a package where it was delivered as a sterilized product. As seen in FIG. 15A, end 52 (see FIG. 6) of bag 50 is opened before insertion of a vial into bag 50 and an unwrapped swab 190 (e.g. an alcohol swab) may be dropped into bag 50 for later use. Then, see FIG. 15B, bag 50 is opened to be disposed about a vial 192. Vial 192 is then preferably displaced without hand contact into bag 50 which is then sealed. It is recommended that the seal be tested by a slight squeeze to assure there is no leakage.

Figure 15C:
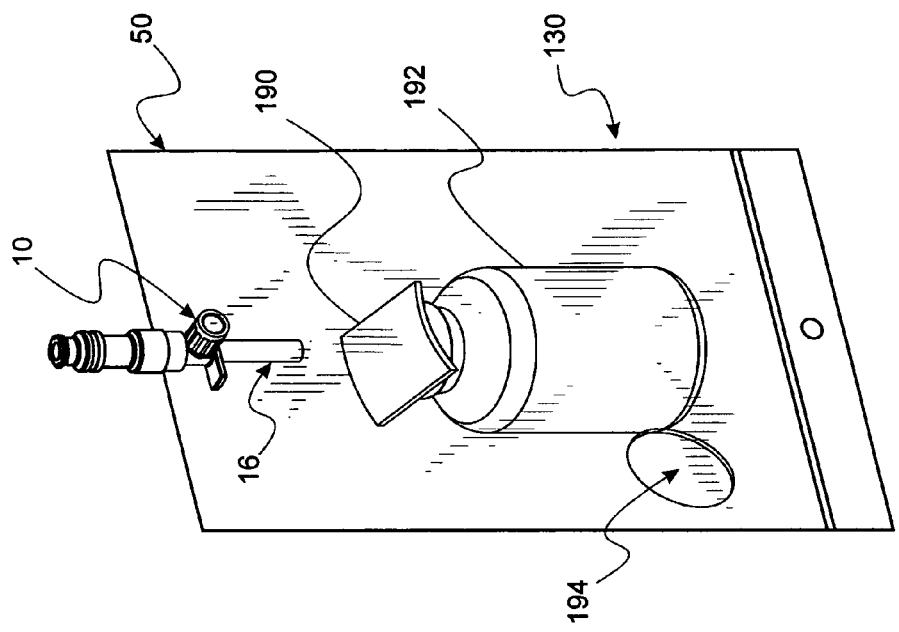
FIG. 15C is a perspective of the subassembly of FIG. 15B with vial fully inserted and zipper seal closed and a vial cap about to be removed.
Figure 15D:
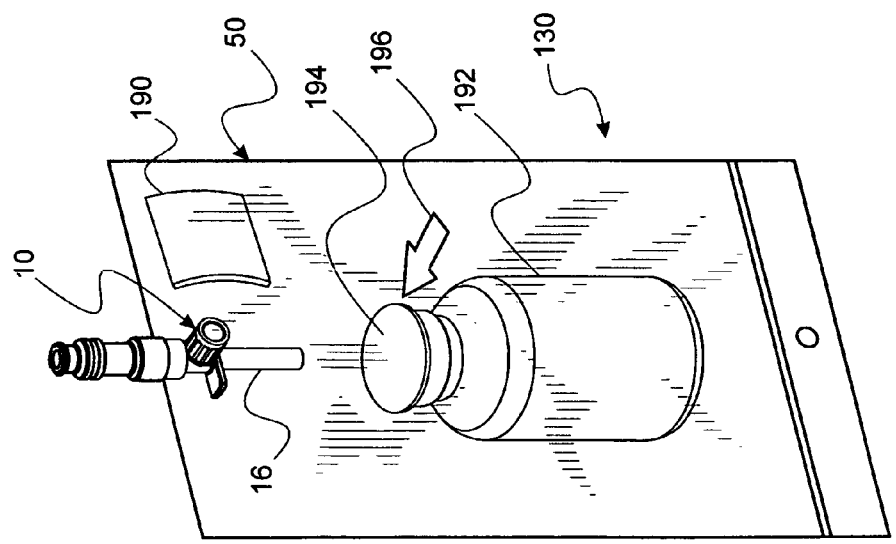
FIG. 15D is a perspective of the subassembly of FIG. 15C with vial cap removed and swab in place to disinfect the vial septum.
Figure 15E:
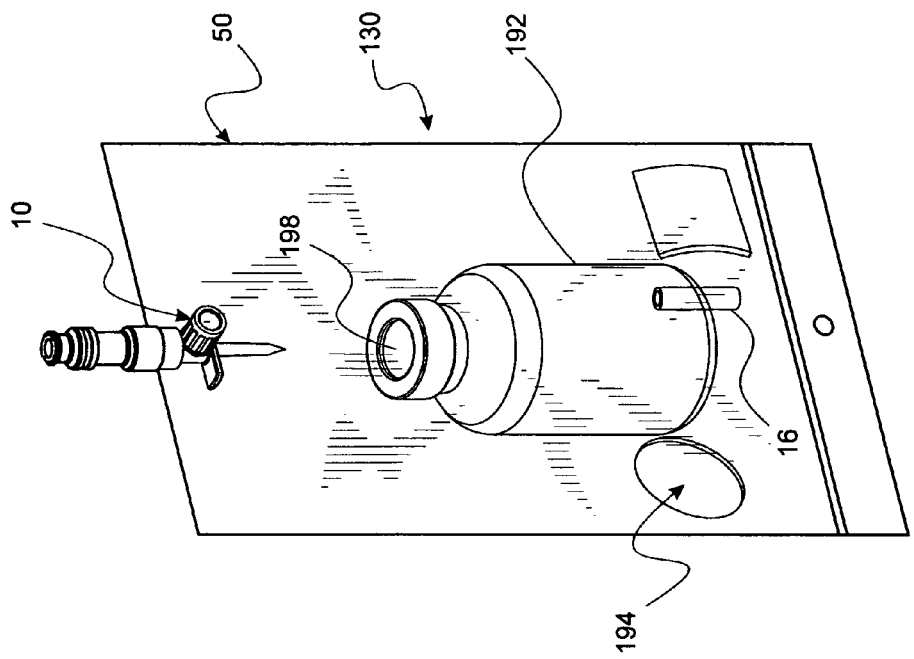
FIG. 15E is a perspective of the subassembly of FIG. 15D showing vial adapter spike cap in position to be removed.
Figure 15F:
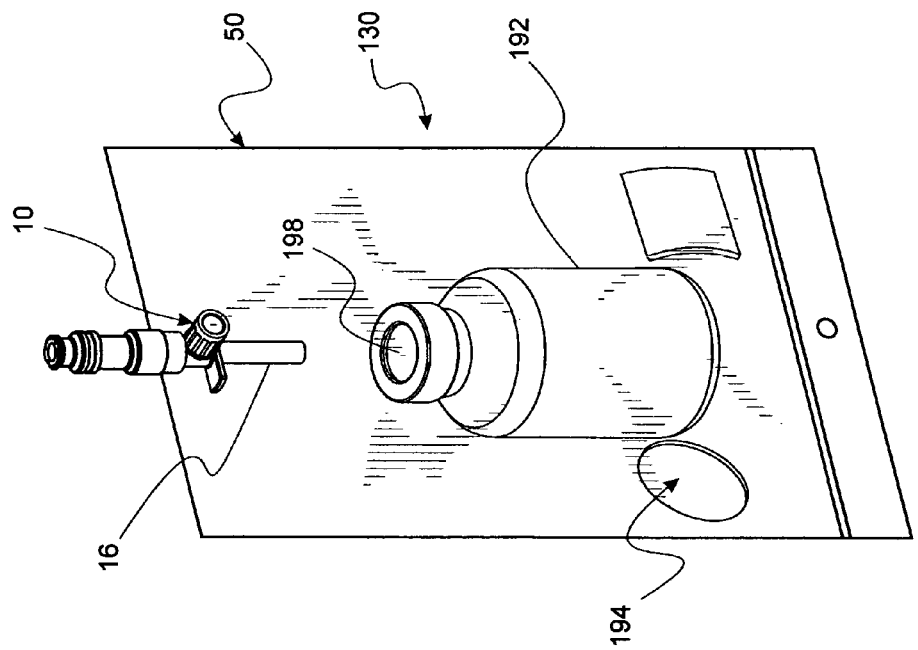
FIG. 15F is a perspective of the subassembly of FIG. 15E with vial cap removed and vial adapter spike disposed for spiking vial septum.
Figure 15G:
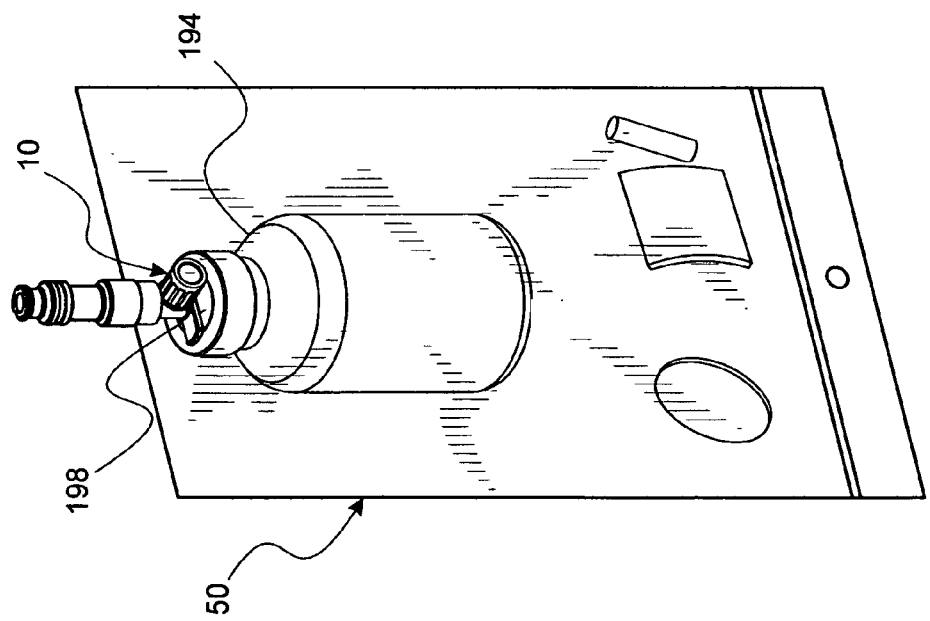
FIG. 15G is a perspective of the subassembly of FIG. 15F with vial adapter spike fully inserted through vial septum.
Figure 18:
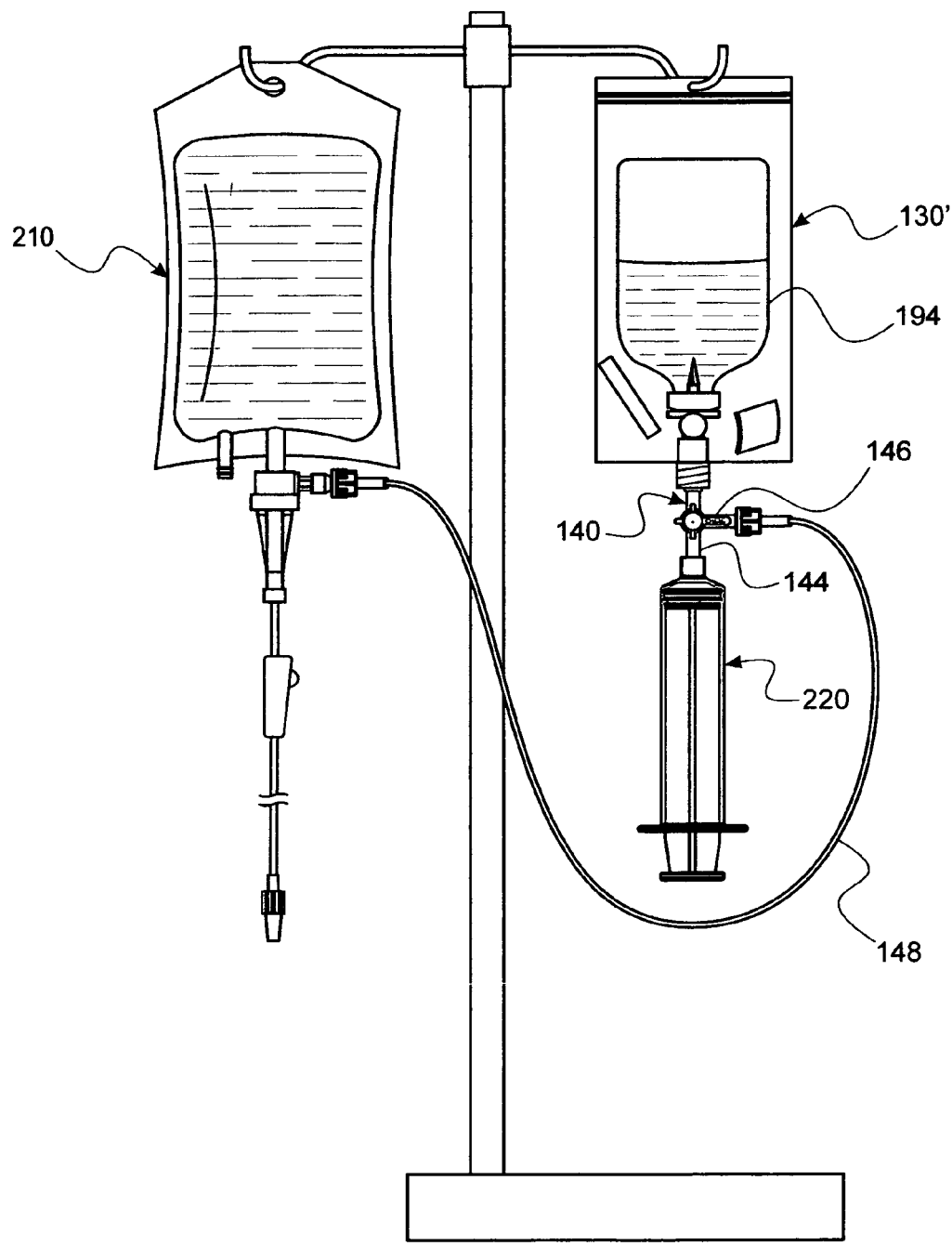
FIG. 18 is a frontal perspective of the subassembly seen in FIG. 14 with a vial inserted into the subassembly bag and spiked and the associated extension set connected to an IV container to complete an operating assembly.

Note that vial 192 generally has a vial cap 194 (see FIG. 5B). If not removed before, vial cap 194 can be removed within bag 50 by applying finger pressure in direction of arrow 196, as seen in FIG. 15C. Once cap 194 is removed, swab 190 can be used to cleanse the septum of vial 194 as seen in FIG. 15D. After cleansing the septum of vial 192, cover 16 is removed form vial adapter 10 by telescoping bag 50 grabbing cover 16 through bag 50 and extending bag 50 to separate vial adapter 10 from cover 16, see FIGS. 15E and 15F. With cover 16 removed, the septum 198 of vial 194 is spiked as seen in FIG. 15G.

Figure 17:
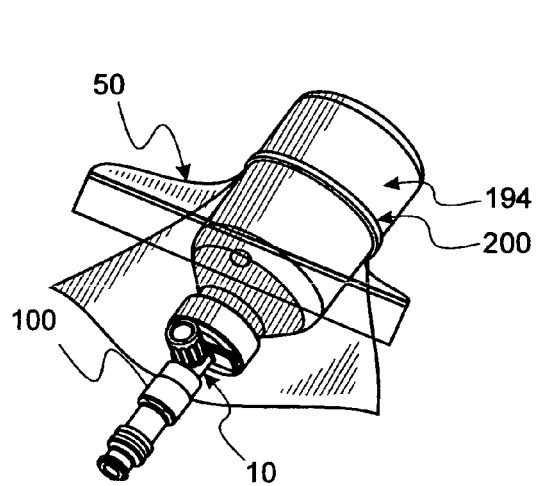
FIG. 17 is a perspective of the subassembly seen in FIG. 15 with the bag tightly folded and held in place by an elastic band to secure and stabilize the vial relative to the vial adapter and spike to complete an operating assembly.

Because vial adapter 10 is without flanges or latch arms for stabilizing a vial, vial adapter 10 may be used with a large variety of vial sizes (independent of vial collar-top size). It is noted that flanges or latch arms are well known in vial handling art to provide support to stabilize a spiked vial. To provide a reasonable substitute for such support, bag 50 is tightly folded about the vial (such as vial 194) and an elastic band 200 (earlier disclosed as part of the convenience kit assembly) is tightly bound about bag 50 and vial 194 as seen in FIG. 17. By means of such binding, vial 194 is clearly stable for hand held operation and no vial supporting flanges or latch arms are required. In this configuration, needleless connector 100 may be affixed to a syringe (preferably through a needleless connector adapter) and a dose measured and transferred by procedures which are commonly used contemporarily. However, such is done with added safety due to complete enclosure of vial 194 by bag 50.

Figure 16:
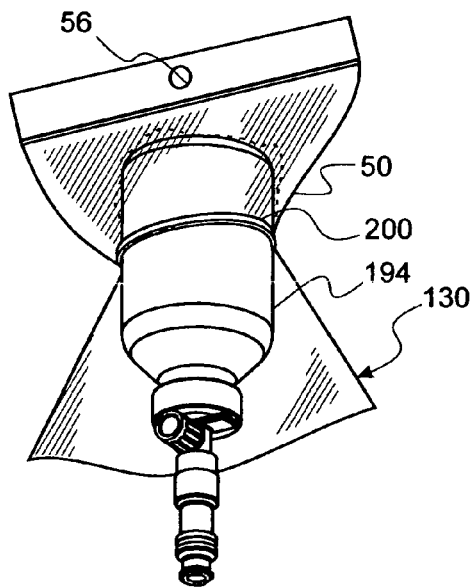
FIG. 16 is a perspective of the subassembly seen in FIG. 15 with an elastic band secured about bag and vial to provide stability for the vial within the bag while the bag is hung for hands free use.

If it is desired to hang a bag and use a subassembly (such as subassembly 130) and associated parts in a hands free mode, elastic band 200 may be disposed about bag 50 and vial 194 as seen in FIG. 16. Subassembly 130', hung for hands free operation, is seen coupled to a target IV container 210 in FIG. 18. Note that a syringe 220 is affixed to stopcock 140 portal 144. Extension set 148 is connected through portal 146. In a first path stopcock selected state, syringe 220 is connected to communicate with bidirectional flow with contents of vial 194 to fill syringe 220 with a desired measured dose while returning unwanted fluid into vial 194. In a second path stopcock selected state, contents of syringe 220 are dispensed into target IV container 210 through extension set 148. Note that the so joined system is entirely closed during vial access, dose measurement and dose delivery.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A method for making a sealable vial adapter enclosing safety shield convenience kit comprising the steps of:
    (a) providing:
        (i) a vented vial adapter having a vial spike for piercing a vial septum on one end and a fluid dispensing portion on the opposite end thereof, said fluid dispensing portion comprising a hollow cylindrical tube comprising internal geometry consistent with a female luer fitting and distally disposed outwardly protruding flanges structured for mating with a male luer locking connector and further comprising a cylindrical outer surface of predetermined length and diameter proximally disposed relative to said flanges;
        (ii) a fluid communicating device comprising a male luer part which further comprises a luer locking connector and associated male luer fitting which provides a luer locking interface for flanges and geometry of said female luer fitting, said luer locking interface comprising a hollow cylindrical shape of predetermined radial diameter;
        (iii) a hollow cylindrical elastic gasket having an internal diameter which is sized to fit tightly about said outer surface when relaxed but having sufficient elasticity to be stretched without permanent deformation to be displaced over said flanges, said gasket having proximal and distal edges which define a length which is less than the predetermined length of the cylindrical outer surface of the dispensing portion and a wall thickness which is sized to contact circumferentially said luer locking interface;
        (iv) a plastic bag comprising a top opening having a close-able seal which provides for complete bag closure at an otherwise open end of the bag and further comprising an otherwise closed bag including the bag bottom at an end opposite the top opening; and
        (v) a bag puncture and gasket expander tool by which said gasket is elastically expanded to be displaced over the flanges to be disposed upon said cylindrical outer surface;
    (b) disposing said vented vial adapter such that access is permitted to the dispensing portion;
    (c) disposing the puncture and expander tool in communication with the dispensing portion;
    (d) forcibly displacing the gasket over said puncture and expander tool such that the gasket is elastically expanded and thereby displaced over the flanges of the dispensing portion to be thereby disposed in a relaxed state in tight communication with said outer surface such that the distal edge thereof is sufficiently close to the flanges to impedingly communicate with a the male luer locking connector when affixed to the flanges;
    (e) creating a hole in the bag bottom which is sufficiently large to permit the bag to be displaced over the flanges yet which is smaller than the diameter of the cylindrical outer surface of the gasket such that, when gasket and hole are compressibly disposed together, the distal edge of the gasket entirely overlays the circumference of the hole;
    (f) displacing said dispensing portion and associated flanges through the hole in the bag until the bag is in contact with the gasket;
    (g) disposing the male luer fitting into the female luer fitting to make a secure fluid tight connection; and
    (h) securely affixing the luer locking connector in tight communication with the flanges thereby forcing the gasket proximally against frictional forces to assure a sealing interface between said luer locking connector, bag and gasket to ensure, after closing the seal of said bag and then spiking a vial with the vial spike, vial originated effluents, other than fluid delivered through luer fittings of said fluid dispensing portion, are fully contained within said bag.

2. A method for making a sealable vial adapter safety shield according to claim 1 wherein the fluid communicating device providing step comprises providing a needleless connector which provides a valve for selectively permitting bidirectional fluid flow through said dispensing portion and of which the luer locking connector is an integral part.

3. A method for making a sealable vial adapter safety shield according to claim 1 wherein the fluid communicating device providing step comprises providing a stopcock which provides a valve for selectively permitting bidirectional fluid flow through said dispensing portion and of which the luer locking connector is an integral part.

4. A method for making a sealable vial adapter safety shield according to claim 3 wherein the fluid communicating device providing step comprises providing an extension set affixed to said stopcock whereby fluid is directly delivered from a vial to a receiving IV container without disconnecting those parts communicating with an associated vial.

5. A method for making a sealable vial adapter safety shield according to claim 1 wherein the gasket providing step comprises providing a gasket made from medical grade PVC tubing.

6. A method for making a sealable vial adapter safety shield according to claim 1 wherein said bag providing step comprises providing a bag with a hang hole.

7. A method for making a sealable vial adapter safety shield according to claim 1 wherein bag providing step comprises providing a bag with a zipper seal.

8. A method for making a sealable vial adapter safety shield according to claim 1 wherein the hole creating step comprises using said puncture and expander tool to puncture the bag bottom to provide the hole in the bag bottom.

9. A method for making a sealable vial adapter safety shield according to claim 1 wherein the gasket using step comprises applying adhesive to the dispensing portion outer surface at the site where the gasket is disposed to create a unitized structure between the gasket and dispensing portion.

10. A method for making a sealable vial adapter safety shield according to claim 1 wherein the luer locking connector affixing step comprises applying adhesive to securely affix the luer locking connector to the flanges, creating a unitized structure, thereby.

11. A method for making a sealable vial adapter safety shield according to claim 1 wherein the gasket providing step comprises severing a gasket of predetermined length from PVC tubing having desired predetermined internal diameter and wall thickness.

12. A method for making a sealable vial adapter enclosing safety shield convenience kit comprising the steps of:
  (a) providing:
    (i) a vial adapter having a vial spike for piercing a vial septum on one end and a fluid dispensing portion on the opposite end thereof, said fluid dispensing portion comprising a hollow cylindrical tube comprising internal geometry consistent with a female luer fitting and distally disposed outwardly protruding flanges structured for mating with a male luer locking connector and further comprising a cylindrical outer surface of predetermined length and diameter proximally disposed relative to said flanges;
    (ii) a fluid communicating device comprising a male luer part which further comprises a luer locking connector and associated male luer fitting which provides a luer locking interface for flanges and geometry of said female luer fitting, said luer locking interface comprising a hollow cylindrical shape of predetermined radial diameter;
    (iii) a hollow cylindrical elastic gasket having an internal diameter which is sized to fit tightly about said outer surface when relaxed but having sufficient elasticity to be stretched without permanent deformation to be displaced over said flanges, said gasket having proximal and distal edges which define a length which is less than the predetermined length of the cylindrical outer surface of the dispensing portion and a wall thickness which is sized to contact circumferentially said luer locking interface;
    (iv) a plastic bag comprising a top opening having a close-able seal which provides for complete bag closure at an otherwise open end of the bag and further comprising an otherwise closed bag including the bag bottom at an end opposite the top opening; and
    (v) bag puncture and gasket expander tooling by which said gasket is elastically expanded to be displaced over the flanges to be disposed upon said cylindrical outer surface and bag is subsequently punctured;
  (b) disposing said vented adapter such that access is permitted to the dispensing portion;
  (c) disposing said puncture and expander tooling in communication with the dispensing portion;
  (d) forcibly displacing the gasket over said puncture and expander tooling such that the gasket is elastically expanded and thereby displaced over the flanges of the dispensing portion to be thereby disposed in a relaxed state in tight communication with said outer surface such that the distal edge thereof is sufficiently close to the flanges to compressively communicate with a the male luer locking connector when affixed to the flanges;
  (e) using said puncture tooling to create a hole in the bag bottom which is sufficiently large to permit the bag to be displaced over the flanges yet which is smaller than the diameter of the cylindrical outer surface of the gasket such that, when gasket and hole are compressibly disposed together, the distal edge of the gasket entirely overlays the circumference of the hole;
  (f) displacing said dispensing portion and associated flanges through the hole in the bag until the bag is in contact with the gasket;
  (g) disposing the male luer fitting into the female luer fitting to make a secure fluid tight connection; and
  (h) securely affixing the luer locking connector in tight communication with the flanges thereby forcing the gasket proximally against frictional forces to assure a sealing interface between said luer locking connector, bag and gasket to ensure, after closing the seal of said bag and then spiking a vial with the vial spike, vial originated effluents, other than fluid delivered through luer fittings of said fluid dispensing portion, are fully contained within said bag.

13. A method for making a sealable vial adapter enclosing safety shield convenience kit according to claim 12 wherein the vial adapter providing step comprises providing a vented vial adapter.

14. A method for making a sealable vial adapter enclosing safety shield convenience kit according to claim 12 wherein the vial adapter providing step comprises providing a vented vial adapter free of vial cap latch arms.

15. A method for making a sealable vial adapter enclosing safety shield convenience kit according to claim 12 wherein the fluid communicating device providing step comprises providing a needleless connector.

* * * * *